United States Patent
Kelley et al.

(10) Patent No.: US 9,877,936 B2
(45) Date of Patent: Jan. 30, 2018

(54) QUINONE COMPOUNDS FOR TREATING APE1 MEDIATED DISEASES

(71) Applicants: Indiana University Research and Technology Corporation, Indianapolis, IN (US); Apexian Pharmaceuticals, Inc., Indianapolis, IN (US)

(72) Inventors: Mark R. Kelley, Zionsville, IN (US); James H. Wikel, Greenwood, IN (US)

(73) Assignees: INDIANA UNIVERSITY RESEARCH AND TECHNOLOGY CORPORATION, Indianapolis, IN (US); APEXIAN PHARMACEUTICALS, INC., Indianapolis, IN (US)

(*) Notice: Subject to any disclaimer, the term of this patent is extended or adjusted under 35 U.S.C. 154(b) by 26 days.

(21) Appl. No.: 14/921,124

(22) Filed: Oct. 23, 2015

(65) Prior Publication Data

US 2016/0045461 A1 Feb. 18, 2016

Related U.S. Application Data

(63) Continuation of application No. 14/119,949, filed as application No. PCT/US2012/039529 on May 25, 2012, now Pat. No. 9,193,700.

(Continued)

(51) Int. Cl.
| | |
|---|---|
| C07D 211/76 | (2006.01) |
| C07D 295/185 | (2006.01) |
| C07D 295/182 | (2006.01) |
| C07C 259/06 | (2006.01) |
| C07C 235/78 | (2006.01) |

(Continued)

(52) U.S. Cl.
CPC .......... *A61K 31/165* (2013.01); *A61K 31/185* (2013.01); *A61K 31/45* (2013.01); *A61K 31/495* (2013.01); *A61K 31/5375* (2013.01); *C07C 235/78* (2013.01); *C07C 259/06* (2013.01); *C07D 211/76* (2013.01);
(Continued)

(58) Field of Classification Search
CPC ............ C07D 295/182; C07D 295/185; C07D 211/76; C07C 259/06; C07C 235/78
See application file for complete search history.

(56) References Cited

U.S. PATENT DOCUMENTS

| | | | |
|---|---|---|---|
| 4,388,312 A | 6/1983 | Terao et al. | |
| 4,533,554 A | 8/1985 | Terao et al. | |

(Continued)

FOREIGN PATENT DOCUMENTS

| | | |
|---|---|---|
| EP | 0025692 | 3/1981 |
| EP | 0301861 | 2/1989 |

(Continued)

OTHER PUBLICATIONS

Ray et al., Mol Endocrinol, Feb. 2010, 24(2): 391-401.*

(Continued)

*Primary Examiner* — Rebecca L Anderson
(74) *Attorney, Agent, or Firm* — Barnes & Thornburg LLP

(57) ABSTRACT

The invention described herein pertains to compounds and compositions for treating Ape1 mediated diseases. In particular, the invention described herein pertains to quinone compounds and pharmaceutical compositions containing them for treating mediated diseases.

20 Claims, 1 Drawing Sheet

Related U.S. Application Data

(60) Provisional application No. 61/490,141, filed on May 26, 2011.

(51) Int. Cl.
*A61K 31/165* (2006.01)
*C07D 295/192* (2006.01)
*A61K 31/185* (2006.01)
*A61K 31/45* (2006.01)
*A61K 31/495* (2006.01)
*A61K 31/5375* (2006.01)

(52) U.S. Cl.
CPC ..... *C07D 295/185* (2013.01); *C07D 295/192* (2013.01); *C07C 2602/10* (2017.05)

(56) References Cited

U.S. PATENT DOCUMENTS

| | | | |
|---|---|---|---|
| 5,385,942 | A | 1/1995 | Abe et al. |
| 5,627,165 | A | 5/1997 | Glazier |
| 6,433,199 | B1 | 8/2002 | Ono et al. |
| 2010/0297113 | A1 | 11/2010 | Kelley et al. |

FOREIGN PATENT DOCUMENTS

| | | |
|---|---|---|
| EP | 0737671 | 10/1996 |
| JP | H01110624 | 4/1989 |
| WO | WO 1999/048860 | 9/1999 |
| WO | WO 2009/042542 | 4/2009 |
| WO | WO 2009/042544 | 4/2009 |
| WO | WO 2012/022467 | 2/2012 |

OTHER PUBLICATIONS

Evans, Angela R., Melissa Limp-Foster, and Mark R. Kelley. "Going APE over ref-1." Mutation Research/DNA Repair 461.2 (2000): 83-108.
Puglisi, Fabio, et al. "Prognostic role of Ape/Ref-1 subcellular expression in stage I-III breast carcinomas." Oncology reports 9.1 (2002): 11-17.
Thomson, Blythe, et al. "Histology-specific expression of a DNA repair protein in pediatric rhabdomyosarcomas." Journal of pediatric hematology/oncology 23.4 (2001): 234-239.
Robertson, Kent A., et al. "Altered expression of Ape1/ref-1 in germ cell tumors and overexpression in NT2 cells confers resistance to bleomycin and radiation." Cancer research 61.5 (2001): 2220-2225.
Puglisi, Fabio, et al. "Prognostic significance of Ape1/ref-1 subcellular localization in non-small cell lung carcinomas." Anticancer research 21.6A (2000): 4041-4049.
Koukourakis, MI, Giatromanolaki, A, Kakolyris, S et al. Nuclear expression of human apurinic/apyrimidinic endonuclease (HAP1/Ref-1) in head and neck cancer is associated with resistance to chemo-radiotherapy and poor outcome. Int J Radiat Oncol Biol Phys. 2001; 50: 27-36.
Kakolyris, S., et al. "Human AP endonuclease 1 (HAP1) protein expression in breast cancer correlates with lymph node status and angiogenesis." British journal of cancer 77.7 (1998): 1169.
Bobola, Michael S., et al. "Apurinic/apyrimidinic endonuclease activity is elevated in human adult gliomas." Clinical cancer research 7.11 (2001): 3510-3518.
Ziel, Kathryn A., et al. "Ref-1/Ape is critical for formation of the hypoxia-inducible transcriptional complex on the hypoxic response element of the rat pulmonary artery endothelial cell VEGF gene." The FASEB journal 18.9 (2004): 986-988.
Fishel, Melissa L., et al. "Impact of APE1/Ref-1 redox inhibition on pancreatic tumor growth." Molecular cancer therapeutics 10.9 (2011): 1698-1708.
Luo, Meihua, et al. "Role of the multifunctional DNA repair and redox signaling protein Ape1/Ref-1 in cancer and endothelial cells: small-molecule inhibition of the redox function of Ape1." Antioxidants & redox signaling 10.11 (2008): 1853-1867.
PCT International Search Report and Written Opinion, prepared for PCT/US2012/039529, dated Nov. 26, 2013.
Extended EP Search report, prepared for EP Patent Application No. 12790370.6, dated Dec. 15, 2014.
Yabunaka, H. et al., "Hybrid ubiquinone: novel inhibitor of mitochondrial complex III," 2002, Biochimica et Biophysica Acta. Bioenergenetic, 1556, 106-112.
Feng, Tzu-Shean et al., "Effects of highly active novel artemisinin-chloroquinoline hybrid compounds on β-hematin formation, parasite morphology and endocytosis in Plasmodium falciparum," 2011, Biochemical Pharmacology, 82, 236-247.
Tatsuoka, T et al., "Preparation and pharmacological evaluation of 4-(1,4-benzoquinon-2-yl)-4-phenylbutanamides as potential cerebral protective agents," 1992, Chemical and Pharmaceutical Bulletin, 40, 2382-2386.
Salmon-Chemin, L et al., "2- and 3-Substituted 1,4-Naphthoquinone Derivatives as Subversive Substrates of Trypanothione Reductase and Lipoamide Dehydrogenase from Trypanosoma cruzi: Synthesis and Correlation between Redox Cycling Activities and in Vitro Cytotoxicity," 2001, J. Med. Chem., 44, 548-565.
Fukuda, T. et al., "Synthesis of immunologically active muramyl dipeptide derivatives containing a quinonyl moiety via aminoacyl intermediates," Chem. Pharm. Bull., 1981, 29, 2215-2221.
Carpino, L. et al., "Reductive lactonization of strategically methylated quinone propionic acid esters and amides," J. Org. Chem, 1989, 54, 3303-3310.
Suzuki, K. et al., "Preparation and pharmacological evaluation of 1-(1,4-benzoquinon-2-yl)-1,2,3,4-tetrahydronaphthalenes as potent cerebral protective agents," Chem. Pharm. Bull., 1996, 44, 132-138.
Lichtenstein, B. et al., "Reversible proton coupled electron transfer in a peptide-incorporated naphthoquinoneamino acid," Chem. Commun., 2009, 2, 168-170.
Kelley, M. et al., "Functional Analysis of Novel Analogues of E3330 That Block the Redox Signaling Activity of the Multifunctional AP Endonuclease/Redox Signaling Enzyme APE1/Ref-1," Antioxidants & Redox Signaling, 2011, 14, 1387-1401.
Nyland, R. et al., "Design and Synthesis of Novel Quinone Inhibitors Targeted to the Redox Function of Apurinic/Apyrimidinic Endonuclease 1/Redox Enhancing Factor-1 (Ape1/Ref-1)," J. Med. Chem., 2010, 53, 1200-1210.

\* cited by examiner

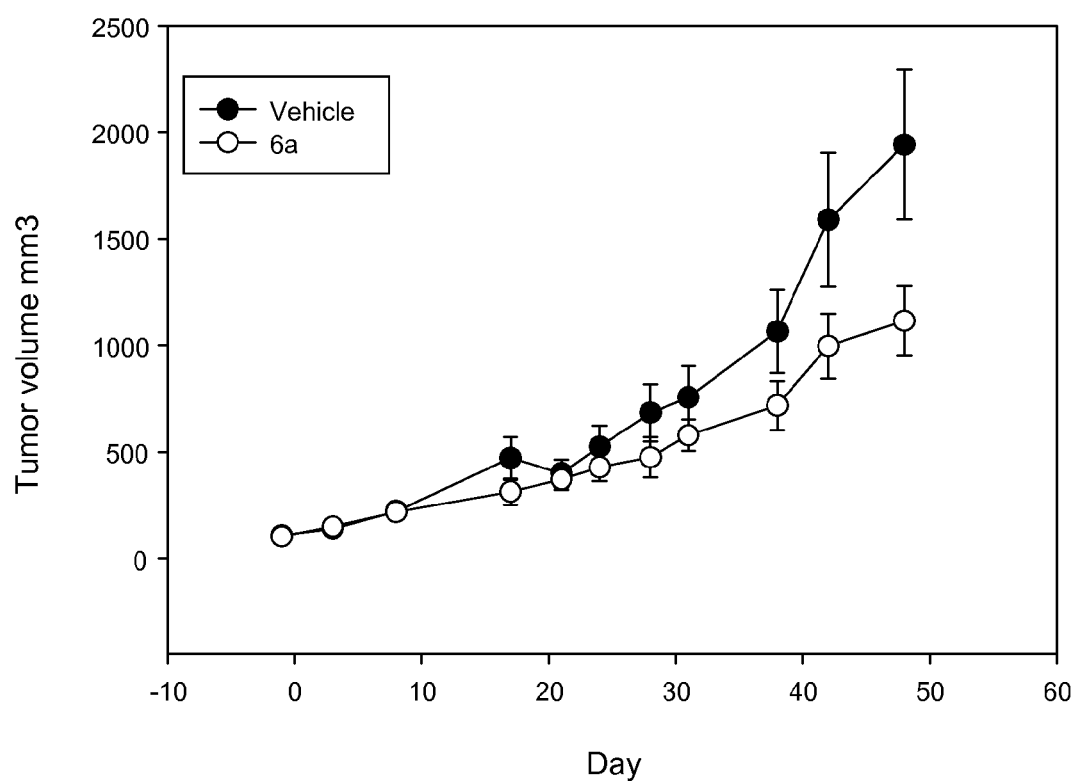

QUINONE COMPOUNDS FOR TREATING APE1 MEDIATED DISEASES

CROSS-REFERENCE TO RELATED APPLICATIONS

This application is a continuation under 35 U.S.C. §120 of U.S. application Ser. No. 14/119,949, filed Nov. 25, 2013, which is a national stage entry under 35 USC §371(b) of PCT International Application No. PCT/US12/39529, filed May 25, 2012, which claims priority under 35 U.S.C. §119(e) to U.S. Provisional Application Ser. No. 61/490,141, filed May 26, 2011, each of which is expressly incorporated by reference herein.

TECHNICAL FIELD

The invention described herein pertains to compounds and compositions for treating Ape1 mediated diseases. In particular, the invention described herein pertains to quinone compounds and pharmaceutical compositions containing them for treating Ape1 mediated diseases.

BACKGROUND AND SUMMARY OF THE INVENTION

Apurinic/apyrimidic endonuclease (Ape1), also known as redox effector factor (Ref-1) (hereinafter Ape1/Ref-1 or Ape1) is an enzyme with a dual role. In addition to its DNA base excision repair (BER) activity, Ape1/Ref-1 also functions as a redox effector maintaining transcription factors in an active reduced state.

Ape1/Ref-1 has been shown to stimulate the DNA binding activity of several transcription factors such as HIF-1α, NFκβ, AP-1 and p53, and others known and unknown, which are reportedly related to tumor survival and progression (Evans et al., *Mutat Res* 2000, 461, 83). Ape1/Ref-1 expression has been shown to be altered in a variety of cancers including breast, cervical, germ cell tumors, adult and pediatric gliomas, osteosarcomas, rhabdomyosarcomas, non-small cell lung cancer, and multiple myeloma (Puglisi et al., *Oncol Rep* 2002, 9, 11; Thomson et al., *Am J Pediatr Hematol Oncol* 2001, 23, 234; Roberston et al., *Cancer Res* 2001, 61, 2220; Puglisi et al., *Anticancer Res* 2001, 21, 4041; Koukourakis et al., *Int J Radiat Oncol Biol Phys* 2001, 50, 27; Kakolyris et al., *Br J Cancer* 1998, 77, 1169; Bobola et al., *Clin Cancer Res* 2001, 7, 3510). High Ape1/Ref-1 expression has also been associated with a poor outcome for chemoradiotherapy, poor complete response rate, shorter local relapse-free interval, poorer survival, and high angiogenesis (Koukourakis et al., *Int J Radiat Oncol Biol Phys* 2001, 50, 27; Kakolyris et al., *Br J Cancer* 1998, 77, 1169; Bobola et al., *Clin Cancer Res* 2001, 7, 3510).

Angiogenesis is an important component of cancer growth and metastasis. The formation of new blood vessels at the site of a cancerous tumor provides a source of nutrients for accelerated tumor growth and expansion as well as a path for tumor cells to enter the bloodstream and spread to other parts of the body. Thus, effective inhibition of angiogenesis is a useful mechanism to slow or prevent the growth and spread of cancer. An increase in Ape1/Ref-1 activity has been associated with angiogenesis. Vascular endothelial growth factor (VEGF) is an important signaling protein involved in both vasculogenesis and angiogenesis. Ape1/Ref-1 is a component of the hypoxia-inducible transcriptional complex formed on the vascular endothelial growth factor (VEGF) gene's hypoxic response element (Ziel et al., *Faseb J* 2004, 18, 986).

In addition to cancer, altered angiogenesis contributes to pathological conditions related to, among others, cardiovascular disease, chronic inflammatory disease, rheumatoid arthritis, diabetic retinopathy, degenerative maculopathy, retrolental fibroplasias, idiopathic pulmonary fibrosis, acute adult respiratory distress syndrome, asthma, endometriosis, psoriasis, keloids, and systemic sclerosis Inhibition of angiogenesis is a desirable clinical outcome for the amelioration or prevention of diseases involving altered angiogenesis.

Given the role the redox site appears to have in pathologies, compounds and compositions for treating the diseases mediated by that site are needed.

It has been discovered that quinone compounds that include a secondary amide or acylhydroxylamine side chain are potent inhibitors of the redox function of Ape1, and therefore useful in treating cancers, and other diseases mediated by Ape1.

In one illustrative embodiment of the invention, compounds of the following formula are described herein:

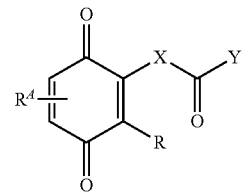

or a pharmaceutically acceptable salt, hydrate, solvate, or morphological form thereof, wherein:

$R^4$ represents two substituents each independently selected from hydrogen and alkoxy, where $R^4$ are not both hydrogen; or $R^4$ represents a fused aryl ring that is optionally substituted;

R is hydrogen or halo, or alkyl, heteroalkyl cycloalkyl, cycloheteroalkyl, alkoxy, heteroalkoxy cycloalkoxy, cycloheteroalkoxy, alkylthio, heteroalkylthio cycloalkylthio, or cycloheteroalkylthio, each of which is optionally substituted;

X is alkylene, alkenylene, or alkynylene, each of which is optionally substituted; and Y is $N(R^1)_2$ or $NR^2OR^2$, where each $R^1$ is independently selected from the group consisting of alkyl heteroalkyl, cycloalkyl, and cycloheteroalkyl, each of which is optionally substituted, or both $R^1$ are taken together with the attached nitrogen to form an optionally substituted heterocycle; where each $R^2$ is independently selected from the group consisting of hydrogen, alkyl heteroalkyl, cycloalkyl, and cycloheteroalkyl, each of which is optionally substituted, and a prodrug group, or both $R^2$ are taken together with the attached nitrogen and oxygen to form an optionally substituted heterocycle.

In addition, various genera and subgenera of the foregoing compounds are described herein. Such genera and subgenera are illustratively defined by various alternative embodiments of the groups $R^4$, R, X, Y, $R^1$, and $R^2$. It is to be understood that all possible combinations of the various genera and subgenera of each of $R^4$, R, X, Y, $R^1$, and $R^2$ are therefore described herein, and represent such additional illustrative embodiments of compounds of the invention. It is to be further understood that each of those additional illustrative embodiments of compounds may be used in any of the compositions, methods, and/or uses described herein.

In another embodiment, pharmaceutical compositions containing one or more of the compounds are also described herein. In one aspect, the compositions include a therapeutically effective amount of the one or more compounds for treating a patient with cancer, or other disease mediated by Ape1. It is to be understood that the compositions may include other component and/or ingredients, including, but not limited to, other therapeutically active compounds, and/or one or more carriers, diluents, excipients, and the like. In another embodiment, methods for using the compounds and pharmaceutical compositions for treating patients with cancer, or other disease mediated by Ape1 are also described herein. In one aspect, the methods include the step of administering one or more of the compounds and/or compositions described herein to a patient with cancer, or other disease mediated by Ape1. In another aspect, the methods include administering a therapeutically effective amount of the one or more compounds and/or compositions described herein for treating patients with cancer, or other disease mediated by Ape1. In another embodiment, uses of the compounds and compositions in the manufacture of a medicament for treating patients with cancer, or other disease mediated by Ape1 are also described herein. In one aspect, the medicaments include a therapeutically effective amount of the one or more compounds and/or compositions for treating a patient with cancer, or other disease mediated by Ape1.

It is appreciated herein that the compounds described herein may be used alone or in combination with other compounds useful for treating diseases mediated by Ape1, including those compounds that may be therapeutically effective by the same or different modes of action. In addition, it is appreciated herein that the compounds described herein may be used in combination with other compounds that are administered to treat other symptoms of diseases mediated by Ape1.

BRIEF DESCRIPTION OF THE DRAWING

FIG. 1 shows the efficacy of compound 6a described herein in decreasing implanted pancreatic tumors compared to untreated control (vehicle).

DETAILED DESCRIPTION

Several illustrative embodiments of the invention are described by the following enumerated clauses:

1. A compound of the formula

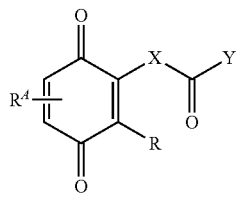

or a pharmaceutically acceptable salt thereof, wherein:

$R^A$ represents two substituents each independently selected from the group consisting of hydrogen and alkoxy, where $R^A$ are not both hydrogen; or $R^A$ represents a fused aryl ring that is optionally substituted;

R is hydrogen or halo, or alkyl, heteroalkyl cycloalkyl, cycloheteroalkyl, alkoxy, heteroalkoxy cycloalkoxy, cycloheteroalkoxy, alkylthio, heteroalkylthio cycloalkylthio, or cycloheteroalkylthio, each of which is optionally substituted;

X is alkylene, alkynylene, or alkynylene, each of which is optionally substituted; and Y is $N(R^1)_2$ or $NR^2OR^2$, where each $R^1$ is independently selected from the group consisting of alkyl heteroalkyl, cycloalkyl, and cycloheteroalkyl, each of which is optionally substituted, or both $R^1$ are taken together with the attached nitrogen to form an optionally substituted heterocycle; where each $R^2$ is independently selected from the group consisting of hydrogen, alkyl heteroalkyl, cycloalkyl, and cycloheteroalkyl, each of which is optionally substituted, and a prodrug group, or both $R^2$ are taken together with the attached nitrogen and oxygen to form an optionally substituted heterocycle.

2. The compound as in clause 1 wherein each $R^A$ is alkoxy.

3. The compound as in clause 1 or 2 wherein each $R^A$ is methoxy.

4. The compound as in clause 1 wherein $R^A$ represents optionally substituted benzo.

5. The compound as in clause 1 or 4 wherein $R^A$ represents benzo.

6. The compound as in any one of the preceding clauses wherein R is hydrogen or halo, or alkyl, heteroalkyl cycloalkyl, or cycloheteroalkyl each of which is optionally substituted;

7. The compound as in any one of the preceding clauses wherein R is alkyl or heteroalkyl, each of which is optionally substituted.

8. The compound as in any one of the preceding clauses wherein R is optionally substituted alkyl.

9. The compound as in any one of the preceding clauses wherein R is alkyl.

10. The compound as in any one of the preceding clauses wherein R is methyl.

11. The compound as in any one of clauses 1 to 8 wherein R is alkoxy.

12. The compound as in any one of clauses 1 to 8 or 11 wherein R is methoxy.

13. The compound as in any one of clauses 1 to 8 wherein R is alkylthio.

14. The compound as in any one of clauses 1 to 8 or 13 wherein R is methylthio.

15. The compound as in any one of clauses 1 to 8 wherein R is halo.

16. The compound as in any one of the preceding clauses wherein X is optionally substituted alkylene.

17. The compound as in any one of the preceding clauses wherein X is an epoxy alkylene.

18. The compound as in any one of the preceding clauses wherein X is optionally substituted alkenylene.

19. The compound as in any one of the preceding clauses wherein X is alkyl substituted alkenylene.

20. The compound as in any one of the preceding clauses wherein X is optionally substituted (E)-alkenylene.

21. The compound as in any one of the preceding clauses wherein X is alkyl substituted (E)-alkenylene.

22. The compound as in any one of the preceding clauses wherein X is alkyl substituted ethenylene.

23. The compound as in any one of the preceding clauses wherein X is $CHCR^X$, and $R^X$ is $C_1$-$C_{10}$ alkyl.

24. The compound as in any one of the preceding clauses wherein $R^X$ is $C_1$-$C_9$ alkyl.

25. The compound as in any one of the preceding clauses wherein $R^X$ is $C_9$ alkyl.

26. The compound as in any one of the preceding clauses wherein $R^X$ is n-nonyl.

27. The compound as in any one of the preceding clauses wherein $R^X$ is $C_1$-$C_6$ alkyl.

28. The compound as in any one of the preceding clauses wherein $R^X$ is $C_1$-$C_4$ alkyl.

29. The compound as in any one of the preceding clauses wherein $R^X$ is $C_3$-$C_4$ alkyl.

30. The compound as in any one of the preceding clauses wherein $R^X$ is methyl.

31. The compound as in any one of the preceding clauses wherein each $R^1$ is optionally substituted alkyl.

32. The compound as in any one of the preceding clauses wherein each $R^1$ is alkyl.

33. The compound as in any one of the preceding clauses wherein each $R^1$ is methyl.

34. The compound as in any one of clauses 1 to 31 wherein at least one $R^1$ is hydroxyalkyl.

35. The compound as in any one of clauses 1 to 31 or 34 wherein one $R^1$ is hydroxyalkyl.

36. The compound as in any one of clauses 1 to 31 wherein at least one $R^1$ is polyhydroxyalkyl.

37. The compound as in any one of clauses 1 to 31 or 36 wherein one $R^1$ is polyhydroxyalkyl.

38. The compound as in any one of clauses 1 to 31, 36, or 37 wherein one $R^1$ is pentahydroxyhexyl.

39. The compound as in any one of clauses 1 to 30 wherein both $R^1$ are taken together with the attached nitrogen to form an optionally substituted heterocycle selected from the group consisting of pyrrolidine, piperidine, piperazine, morpholine, pyrrolidinone, piperidinone, piperazinone, and morpholinone.

40. The compound as in any one of clauses 1 to 30 or 39 wherein both $R^1$ are taken together with the attached nitrogen to form an optionally substituted heterocycle selected from the group consisting of piperidine, piperazine, morpholine, and piperidinone.

41. The compound as in any one of clauses 1 to 30, 39 or 40 wherein both $R^1$ are taken together with the attached nitrogen to form an alkyl substituted heterocycle selected from the group consisting of pyrrolidine, piperidine, piperazine, morpholine, pyrrolidinone, piperidinone, piperazinone, and morpholinone.

42. The compound as in any one of clauses 1 to 30, or 39 to 41 wherein both $R^1$ are taken together with the attached nitrogen to form an alkyl substituted piperazine.

43. The compound as in any of the preceding clauses wherein at least one $R^2$ is hydrogen.

44. The compound as in any of the preceding clauses wherein at least one $R^2$ is optionally substituted alkyl.

45. The compound as in any of the preceding clauses wherein at least one $R^2$ is alkyl.

46. The compound as in any one of clauses 1 to 42, 44, or 45 wherein at both $R^2$ are alkyl.

47. The compound as in any one of clauses 1 to 42, or 44 to 46 wherein at both $R^2$ are methyl.

48. The compound as in any one of clauses 1 to 42 wherein both $R^2$ are taken together with the attached nitrogen and oxygen to form an optionally substituted heterocycle selected from the group consisting of oxazolidine, oxazine, oxazapine, oxazolidinone, oxazinone, and oxazapinone.

49. The compound as in any one of clauses 1 to 42, or 48 wherein both $R^2$ are taken together with the attached nitrogen and oxygen to form an optionally substituted heterocycle selected from the group consisting of oxazolidine, oxazine, and oxazapine.

50. A pharmaceutical composition comprising one or more compounds of any one of clauses 1 to 49.

51. A unit dose or unit dosage form composition comprising one or more compounds of any one of clauses 1 to 49 for treating a disease responsive to Ape1 inhibition.

52. The composition or unit dose or unit dosage form of clause 50 or 51 further comprising one or more carriers, diluents, or excipients, or a combination thereof.

53. A method for treating a disease responsive to Ape1 inhibition in a host animal, the method comprising the step of administering to the host animal a composition comprising a therapeutically effective amount of one or more compounds of any one of claims 1 to 19; or a pharmaceutical composition comprising one or more compounds of any one of claims 1 to 19, optionally further comprising one or more carriers, diluents, or excipients, or a combination thereof.

54. The method of clause 53 wherein the host animal is a human.

55. Use of one or more compounds or compositions of any one of clauses 1 to 52 in the manufacture of a medicament for treating a disease responsive to Ape1 inhibition.

56. A compound or composition of any one of clauses 1 to 52 for treating a disease responsive to Ape1 inhibition.

In reciting the foregoing collection of clauses, it is to be understood that all possible combinations of features, and all possible subgenera and subcombination are described. For example, it is to be understood that when $R^A$ is limited to alkoxy, R may be limited to alkyl or heteroalkyl, each of which is optionally substituted, or alternatively, to optionally substituted alkyl, or alternatively, to alkylthio, and so forth. Similarly, when X is limited to alkyl substituted ethenylene, $R^X$ may be limited to n-nonyl, or alternatively, to $C_3$-$C_4$ alkyl, or alternatively, to methyl, and so forth. Similarly, when $R^A$ is limited to benzo, X may be limited to alkyl substituted ethenylene, and $R^1$ may be limited to alkyl, or alternatively, X may be limited to alkyl substituted (E)-alkenylene, and $R^1$ may be limited to polyhydroxyalkyl, or alternatively, X may be limited to $CHCR^X$, where $R^X$ is $C_1$-$C_{10}$ alkyl, and $R^1$ may be limited to methyl, and so forth. Other combinations, subgenera and subcombinations are also described by the collection of clauses.

In each of the foregoing and following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

Illustrative derivatives include, but are not limited to, both those compounds that may be synthetically prepared from the compounds described herein, as well as those compounds that may be prepared in a similar way as those described herein, but differing in the selection of starting materials. It is to be understood that such derivatives may include prodrugs of the compounds described herein, compounds described herein that include one or more protection or protecting groups, including compounds that are used in the preparation of other compounds described herein.

The compounds described herein may contain one or more chiral centers, or may otherwise be capable of existing as multiple stereoisomers. It is to be understood that in one embodiment, the invention described herein is not limited to any particular sterochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may be include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$ and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carboxylate and derivatives thereof" includes the group $CO_2H$ and salts thereof, and esters and amides thereof, and CN.

As used herein, the term "sulfonyl or a derivative thereof" includes $SO_3H$ and salts thereof, and esters and amides thereof.

As used herein, the term "hydroxylamino and derivatives thereof" includes NHOH, and alkyloxylNH alkenyloxylNH alkynyloxylNH heteroalkyloxylNH heteroalkenyloxylNH heteroalkynyloxylNH cycloalkyloxylNH cycloalkenyloxylNH cycloheteroalkyloxylNH cycloheteroalkenyloxylNH aryloxylNH arylalkyloxylNH arylalkenyloxylNH arylalkynyloxylNH heteroaryloxylNH heteroarylalkyloxylNH heteroarylalkenyloxylNH heteroarylalkynyloxylNH acyloxy, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical —$(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N-($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N-($C_1$-$C_6$ alkyl)alkylcarbonylaminoalkyl, cyano, and nitro; or $Z^X$ is selected from —$CO_2R^4$ and —$CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

Illustratively, compounds described herein may be prepared as shown in the following scheme:

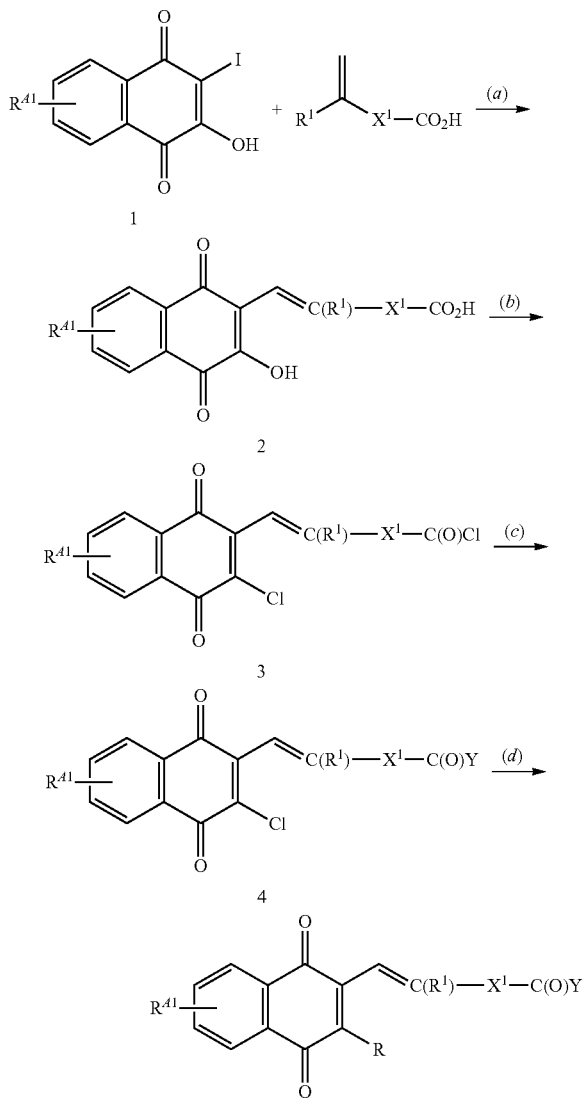

(a) 1. Pd(II)OAc, base, $H_2O$; 2. acid; (b) $(COCl)_2$, DMF, $CH_2Cl_2$; (c) Y-H, optional base; (d) R-H, optional base. Compounds (1) are prepared according to Perez et al., Tetrahedron Lett. 48:3995-98 (2007). In the foregoing scheme, Y and R are as defined herein, and $R^{41}$ represents 1 to 4 optional aryl substituents; and the divalent radical CH=C($R^1$)-$X^1$ is an embodiment of the group X, as defined herein.

Illustratively, compounds described herein may be prepared as shown in the following scheme:

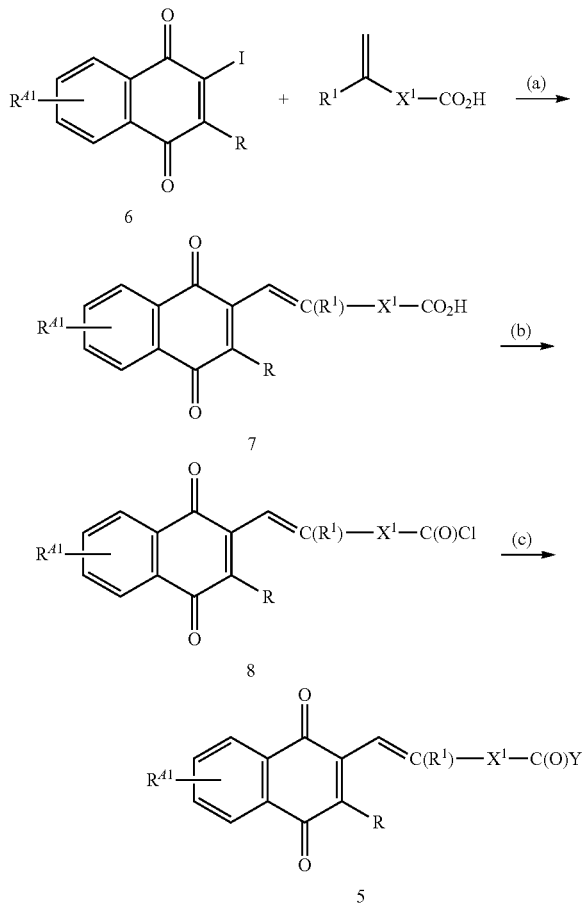

(a) 1. Pd(II)OAc, base, H₂O; 2. acid; (b) (COCl)₂, DMF, CH₂Cl₂;
(c) Y — H, optional base.
In the foregoing scheme, Y and R are as defined herein, and $R^{A1}$ represents 1 to 4 optional aryl substituents; and the divalent radical $CH=C(R^1)-X^1$ is an embodiment of the group X, as defined herein. Alternatively, compounds (5) may be prepared from compounds (7) using conventional amide forming reagents, such as, but not limited to, DCC, EDC, BOP, BOPCl, PyBOP, and the like.

It is to be understood that the compounds of the formula

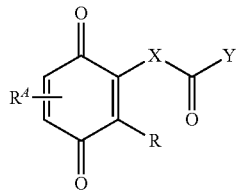

wherein $R^A$ represents two substituents each independently selected from hydrogen and alkoxy, where $R^A$ are not both hydrogen; and R, X, and Y are as defined herein, are prepared using the foregoing processes where the corresponding quinone starting material is used in place of compounds (1) and (6).

Additional compounds described herein are prepared by adapting the processes described in PCT/US2008/077213, the disclosure of which is incorporated herein by reference.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —CO₂H, —NR₂. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylamino ethyl, and the like; 2-(a&oxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, $(C_3-C_{20})$alkanoyl; halo-$(C_3-C_{20})$alkanoyl; $(C_3-C_{20})$alkenoyl; $(C_4-C_7)$cycloalkanoyl; $(C_3-C_6)$-cycloalkyl$(C_2-C_{16})$alkanoyl; optionally substituted aroyl, such as unsubstituted aroyl or aroyl substituted by 1 to 3 substituents selected from the group consisting of halogen, cyano, trifluoromethanesulphonyloxy, $(C_1-C_3)$alkyl and $(C_1-C_3)$alkoxy, each of which is optionally further substituted with one or more of 1 to 3 halogen atoms; optionally substituted aryl$(C_2-C_{16})$alkanoyl and optionally substituted heteroaryl$(C_2-C_{16})$alkanoyl, such as the aryl or heteroaryl radical being unsubstituted or substituted by 1 to 3 substituents selected from the group consisting of halogen, $(C_1-C_3)$alkyl and $(C_1-C_3)$alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, ($C_1$-$C_3$)alkyl, and ($C_1$-$C_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

Illustratively, administering includes local use, such as when administered locally to the site of disease, injury, or defect, or to a particular organ or tissue system. Illustrative local administration may be performed during open surgery, or other procedures when the site of disease, injury, or defect is accessible. Alternatively, local administration may be performed using parenteral delivery where the compound or compositions described herein are deposited locally to the site without general distribution to multiple other non-target sites in the patient being treated. It is further appreciated that local administration may be directly in the injury site, or locally in the surrounding tissue. Similar variations regarding local delivery to particular tissue types, such as organs, and the like, are also described herein. Illustratively, compounds may be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustrative formats for oral administration include tablets, capsules, elixirs, syrups, and the like.

Illustrative routes for parenteral administration include intravenous, intraarterial, intraperitoneal, epidurial, intraurethral, intrasternal, intramuscular and subcutaneous, as well as any other art recognized route of parenteral administration.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

In addition to the illustrative dosages and dosing protocols described herein, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of involvement or the severity of the disease or disorder, the response of the individual patient, the particular compound administered, the mode of administration, the bioavailability characteristics of the preparation administered, the dose regimen selected, the use of concomitant medication, and other relevant circumstances.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form. It is to be understood that one or more carriers, one or more diluents, one or more excipients, and combinations of the foregoing may be used in making the pharmaceutical compositions described herein. It is appreciated that the carriers, diluents, and excipients used to prepare the compositions described herein are advantageously GRAS (generally regarded as safe) compounds.

The effective use of the compounds, compositions, and methods described herein for treating or ameliorating one or more diseases mediated by Ape1 may be based upon animal models, such as murine, canine, porcine, and non-human primate animal models of disease. For example, it is understood that cancer in humans may be characterized by a loss of function, and/or the development of symptoms, each of which may be elicited in animals, such as mice, and other surrogate test animals. In addition, in vitro assays that include one or more cancer cell lines may be used to evaluate the methods of treatment and the pharmaceutical compositions described herein to determine the therapeutically effective amounts described herein.

The following examples further illustrate specific embodiments of the invention; however, the following illustrative examples should not be interpreted in any way to limit the invention.

EXAMPLES

The following additional example compounds are described herein

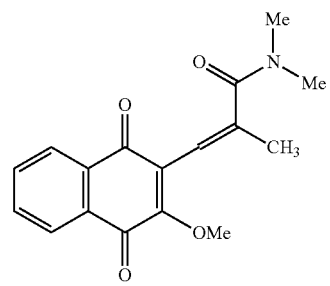

5a

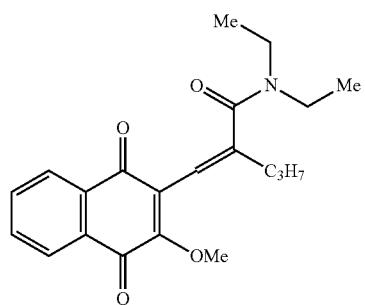

5c

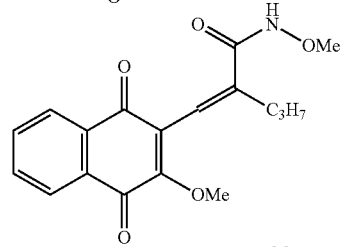

5d

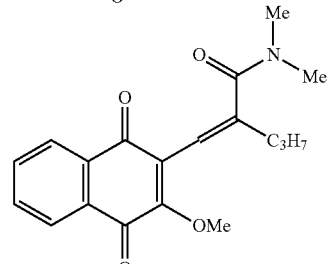

5e

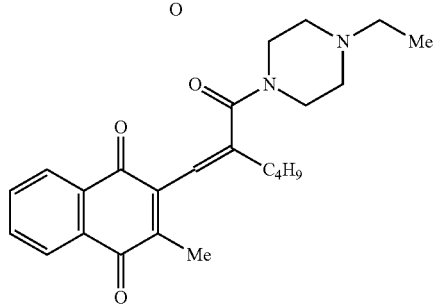

5f

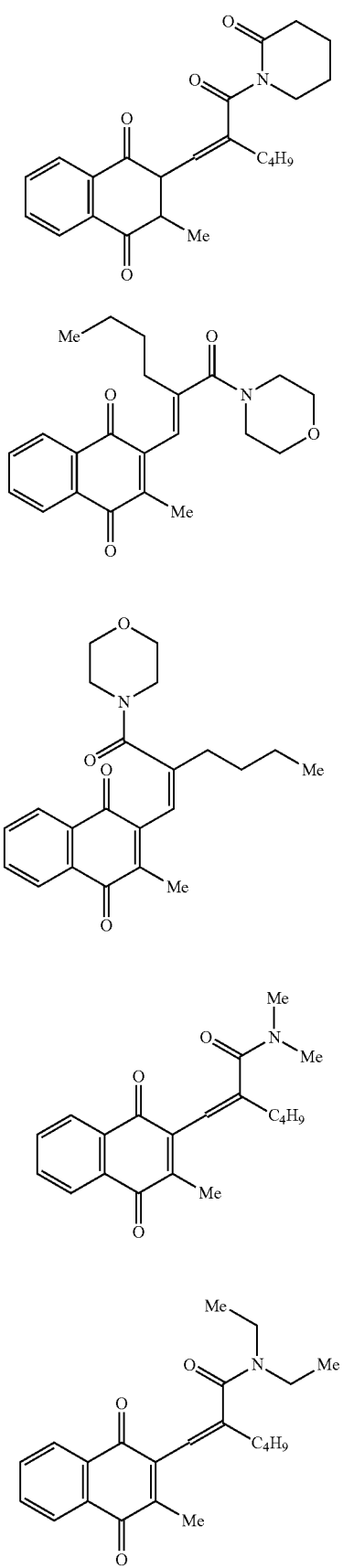
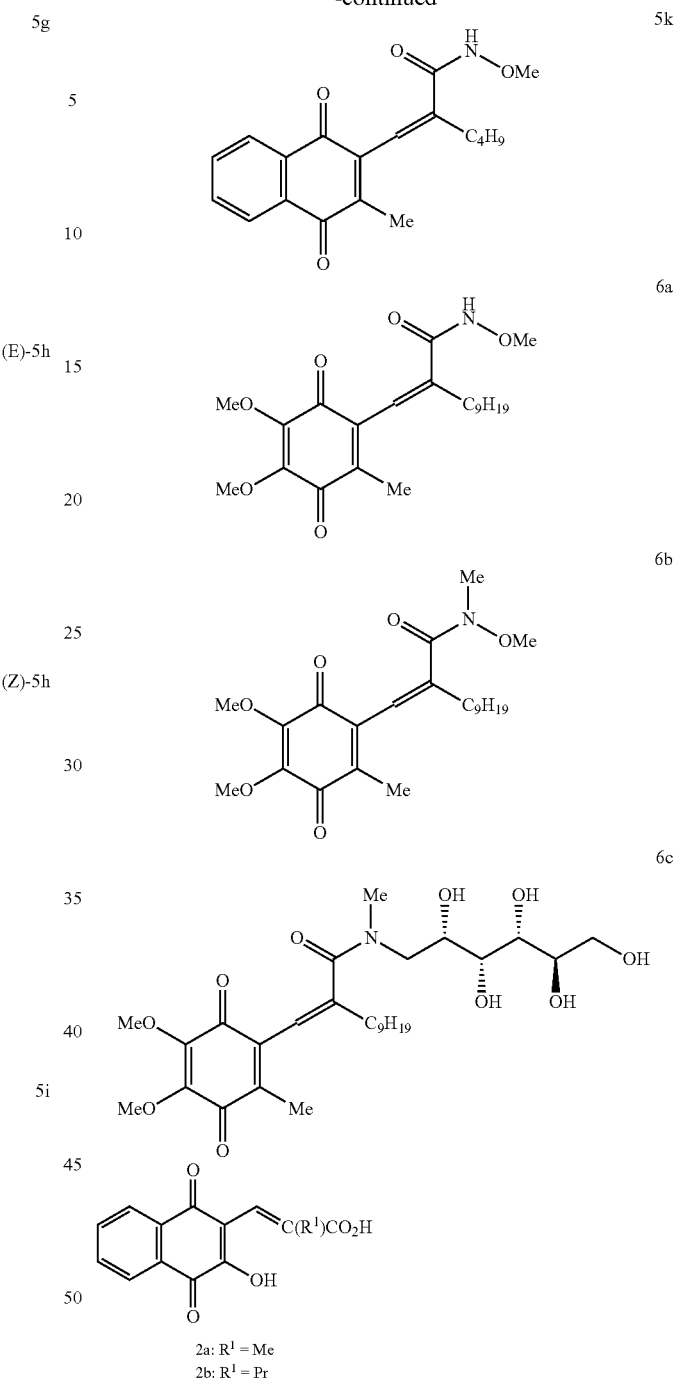

EXAMPLE 2a. In a 2 L 3-necked flask equipped with a mechanical stirrer and a gas dispersion fitted tube was place 2-iodo-3-hydroxy-1,4 naphthoquinone (18 g, 0.06 mol) and methacrylic acid (12.9 g, 0.15 mol) in a solution of potassium carbonate (41.4 g, 0.3 mol) in water (600 mL). The reaction mixture was stirred and sparged with argon for 30 min. Palladium(II)acetate (0.67 g, 0.003 mol) was added and sparging continued for an additional 30 min. The resulting mixture was heated in an oil-bath at 100° C. HPLC analysis showed the reaction was complete after 1 hr. The reaction mixture was cooled to room temperature and the black Pd metal was filtered. The filtrate was placed in a 2 L 3-necked flask equipped with a mechanical stirrer, cooled in an ice-methanol bath and acidified with 50% H3PO4 (160 mL) to pH=2. After stirring for 1 hr, the solid was collected, washed with water (1 L), a mixture of 20% acetone in water (500 mL) and air dried to give 12.6 g (81%) of 2a as a mustard colored solid. HPLC analysis showed a purity of 98%. NMR (d4-MeOH : d6-DMSO ; 1:2) δ 7.6-8.2 (m, 4H), 7.3 (q, 1H), 4.7 (br s, 2H), 1.8 (d, 3H).

EXAMPLE 2b. Similarly, 2b was prepared in 72% yield. NMR (d6-DMSO) δ 12.6 (br s, 1H), 11.65 (br s, 1H), 8.0 (m, 2H), 7.8 (m, 2H), 7.15 (s, 1H), 2.1 (m, 2H), 1.4 (m, 2H), 0.8 (m, 3H).

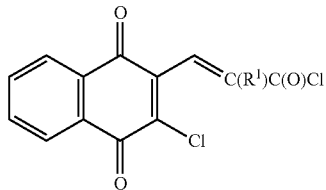

3a: $R^1$ = Me
3b: $R^1$ = Pr

EXAMPLE 3a. To a suspension of 2a (3.61 g, 0.014 mol) and DMF (0.1 mL) in dichloromethane (75 mL) was added oxalyl chloride (17.5 mL of 2M in CH2Cl2, 0.035 mol) over 20 min at room temperature. The resulting mixture was stirred at room temperature over night and then was concentrated under reduced pressure to give 4.1 g (100%) 3a as a brown solid. This solid was used directly in the next step. NMR (CDCl3) δ 7.8-8.2 (m, 2H), 7.7-7.8 (m, 2H), 7.65 (q, 1H), 1.9 (d, 3H).

EXAMPLE 3b. Similarly, 3b was prepared. NMR (CDCl3) 67 7.8-8.2 (m, 2H), 7.7-7.8 (m, 2H), 7.4 (s, 1H), 2.1-2.4 (m, 2H), 1.2-1.7 (m, 2H), 0.6-1.0 (m, 3H).

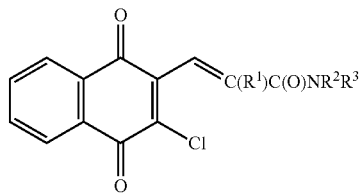

4a: $R^1$ = Me, $R^2$ = $R^3$ = Me
4b: $R^1$ = Me, $R^2$ = H, $R^3$ = Me
4c: $R^1$ = Pr, $R^2$ = $R^3$ = Et
4d: $R^1$ = Pr, $R^2$ = H, $R^3$ = OMe
4e: $R^1$ = Pr, $R^2$ = $R^3$ = Me

EXAMPLE 4a. To a solution of crude 3a (8.85 g, 0.03 mol) in dichloromethane (50 mL) was a solution of dimethyl amine hydrochloride (3.67 g, 0.945 mol) and diisopropyl amine (11.6 g, 0.09 mol) in dichloromethane (50 mL) at room temperature over 45 min. HPLC analysis after 15 min showed the reaction was complete. The reaction mixture was washed with water (100 mL), 1M HCl (2×100 mL), brine (100 mL), filtered through 1PS filter paper and concentrated under reduced pressure to give 8.8 g of a deep red solid. The solid was flash chromatographed over silica gel (150 g) with anhydrous sodium sulfate (20 g) on top packed with hexane. The column was eluted with 125 mL portions of 15% ethyl acetate in hexane for fractions 1-4, 25% ethyl acetate in hexane for fractions 5-8, 35% ethyl acetate in hexane for fractions 9-16, and 50% ethyl acetate in hexane for fractions 17-32. All fractions were checked by TLC (ethyl acetate: hexane; 1:1) and some fractions by HPLC. The product was eluted in fractions 21 to 30. They were combined and concentrated under reduced pressure to give 6.5 g of an orange solid. This solid was suspended over 15% ethyl acetate in hexane (50 mL) and stirred for 15 min. The solid was collected and air dried to give 6.1 g (67%) of 4a as an orange solid. HPLC analysis showed a purity of 99%. NMR (CDCl3) δ 7.9-8.2 (m, 2H), 7.5-7.8 (2H), 6.5 (q, 1H), 3.1 (br s, 6H), 1.9 (d, 3H).

EXAMPLE 4b. Similarly, 4b (67%) was prepared. NMR (CDCl3) δ 7.9-8.2 (m, 2H), 7.6-7.8 (m, 2H), 6.9 (q, 1H), 6.3 (br s, 1H), 2.9 (d, 3H), 1.9 (d, 3H).

EXAMPLE 4c. Similarly, 4c (62%) was prepared. NMR (CDCl3) δ 8.1-8.3 (m, 2H), 7.7-7.8 (m, 2H), 6.1 (s, 1H), 3.6 (br d, 4H), 2.2 (t, 2H), 1.45 (m, 2H), 1.25 (br s, (6H), 0.9 (t, 3H).

EXAMPLE 4d. Similarly, 4d (73%) was prepared. NMR (CDCl3) δ 8.85 (s, 1H), 8.25 (m, 2H), 8.1 (m, 2H), 6.65 (br s, 1H), 3.9 (s, 3H), 2.2 (t, 2H), 1.5 (m, 2H), 0.85 (t, 3H).

EXAMPLE 4e. Similarly, 4e (59%) was prepared. NMR (CDCl3) δ 7.9-8.2 (m, 2H), 7.6-7.8 (m, 2H), 6.1 (s, 1H), 3.2 (br d, 2H), 2.3-(t, 2H), 1.2-1.7 (m, 2H), 0.9 (t, 3H).

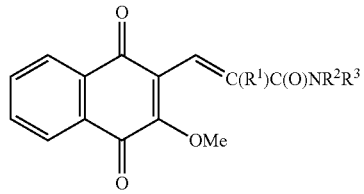

5a: $R^1$ = Me, $R^2$ = $R^3$ = Me
5b: $R^1$ = Me, $R^2$ = H, $R^3$ = Me
5c: $R^1$ = Pr, $R^2$ = $R^3$ = Et
5d: $R^1$ = Pr, $R^2$ = H, $R^3$ = OMe
5e: $R^1$ = Pr, $R^2$ = $R^3$ = Me

EXAMPLE 5a. To a solution of 4a (4.25 g, 0.014 mol) in methanol (100 mL) was added a solution of sodium methoxide in methanol (4.2 mL of 5M) in one portion under argon. The reaction mixture was acidified to pH=3 by using 3M HCl (3.5 mL), and then was concentrated under reduced pressure. The resulting residue was dissolved in ethyl acetate (150 mL), washed with water (2×75 m), brine (1×100 mL), filtered through 1PS filter paper and concentrated under reduced pressure to give 4.2 g an oil which solidified. This solid was triturated with hexane (50 mL) for 30 min and the solid was collected and air dried to give 3.8 g (86%) of 5a (86%) as a light orange solid. HPLC analysis showed a purity of 100%. NMR (CDCl3) δ 8.1 (m, 2H), 7.8 (m, 2H), 6.3 (s, 1H), 4.15 (s, 3H), 3.2 (br d, 6H), 1.8 (s, 3H).

EXAMPLE 5c. Similarly, 5c (96%) was prepared. HPLC analysis showed a purity of 99%. NMR (CDCl3) δ 8.15 (m, 2H), 7.75 (m, 2H), 6.2 (s, 1H), 4.1 (s, 3H), 3.6 (br d, 4H), 2.2 (t, 2H), 1.4 (m, 4H), 1.25 (br d, 4H), 0.85 (t, 3H).

EXAMPLE 5d. Similarly, 5d (83%) was prepared. HPLC analysis showed a purity of 99%. NMR (CDCl3) δ 8.1 (m, 2H), 7.75 (m, 2H), 6.65 (s, 1H), 4.15 (s, 3H), 3.9 (, 3H), 2.2 (t, 2H), 1.45 (m, 2H), 0.85 (t, 3H).

EXAMPLE 5e. Similarly, 5e was prepared. HPLC analysis showed a purity of 100%. NMR (CDCl3) δ 8.15 (m, 2H), 7.8 (m, 2H), 6.2 (s, 1H), 4.15 (s, 3H), 3.2 (br d, 6H), 2.2 (t, 2H), 1.45 (m, 2H), 0.9 (t, 3H).

COMPARATIVE EXAMPLE 5b. Similarly, 5b (94%) was prepared. HPLC analysis showed a purity better than 93%. NMR (CDCl3) δ 8.1 (m, 2H), 7.75 (m, 2H), 7 (s, 1H), 6.1 (br s, 1H), 4.1 (s, 3H), 2.95 (d, 3H), 1.85 (s, 3H).

In each of the foregoing examples, as well as throughout the description herein, it is to be understood that the geometry of the double bond may be (E), (Z), or any mixture thereof, unless indicated otherwise. For example, (Z)-5h corresponds to the (Z) isomer, and (E)-5h corresponds to the (E) isomer of the double bond.

EXAMPLE. Redox EMSA Assay. Conventional electrophoresis measuring Ape1 expression with 0.02 mM DTT is used to evaluate test compounds. Compound 6a showed improved expression knock-down compared to E3330 (comparative example) in vitro. Compound 6a showed significant signal reduction at 20 μM, while E3330 showed significant signal reduction at 30 μM. Additional details are described in Fishel et al. Mol Cancer Ther. 2011 September; 10(9):1698-708 & Luo et al., Antioxid Redox Signal. 2008 November;10(11):1853-67.

EXAMPLE. Ape1/Ref1 Transcription Factor Activation. The DNA base excision-repair pathway is responsible for the repair of DNA damage caused by oxidation/alkylation and protects cells against the effects of endogenous and exogenous agents. Removal of the damaged base creates a baseless (AP) site. AP endonucleasel (Ape1) acts on this site to continue the BER-pathway repair. Failure to repair baseless sites leads to DNA strand breaks and cytotoxicity. In addition to the repair role, Ape1 also functions as a major redox-signaling factor to reduce and activate transcription factors such as AP1, p53, HIF-$1_{alpha}$, and others that control the expression of genes important for cell survival and cancer promotion and progression. Thus, the Ape1 protein interacts with proteins involved in DNA repair, growth-signaling pathways, and pathways involved in tumor promotion and progression. Test compounds are evaluated for activity in decreasing transactivation of transcription factors. Compound 6a showed significant decrease in % transactivation of NFκB in Hey-C2, SF767, Panc1, and Skov-3X cells lines. Compound 6a was approximately 5-fold to 10-fold more active than E3330 (comparative example) in the four cell lines.

EXAMPLE. Reporter Assay in Cancer Cells. Using lentiviral transcriptional reporter vectors, pGreenFire-NFκB, and pGreenFire-mCMV (negative control), from System Biosciences Inc. (Mountainview, Calif.), HEK293-T cells (Lonza, Inc. Allendale, N.J.) are transfected with the constructs and the media containing the viral supernatants is collected. To generate stably expressing reporter cell lines, cancer cell lines are infected with the viral supernatant and the cells are selected with puromycin (5 ng/mL) for 5 days. For the experiments, test compound is added and left on the cells before being assayed for luciferase activity. SKOV-3X, Panc1, and SF767 cells with the stable pGF-NFκB are treated with test compounds and assayed 40 hrs later for luciferease activity. Panc1 is a pancreatic cancer cell line; SF767 is the glioma cell line. IC$_{50}$ values for test compounds are determined.

| Example | Panc1 IC$_{50}$ | Glioma IC$_{50}$ |
|---|---|---|
| 5a | 5 μM | 10 μM |
| 5c | 8μ | 18 μM |
| 5d | 7μ | 10 μM |
| 5e | 5 μM | 9 μM |
| 6a | 9 μM | 12 μM |
| 6b | 10 μM | 18 μM |
| E3330 (comparative example) | 52 μM | 80 μM |

EXAMPLE. Growth Inhibition of Cancer Cells. Test compounds are assayed for growth inhibition ability against two 2 ovarian cancer cell lines. IC$_{50}$ values for test compounds are determined.

| Example | Hey-C2 IC$_{50}$ | Skov-3X IC$_{50}$ |
|---|---|---|
| 5a | 18 μM | 17 μM |
| 5c | 25 μM | 30 μM |
| 5d | 11 μM | 10 μM |
| 5e | 10 μM | 12 μM |
| 6a | 28 μM | 38 μM |
| 6b | 22 μM | 32 μM |
| E3330 (comparative example) | ~100 μM | ~100 μM |

EXAMPLE. Pharmacokinetics. The pharmacokinetics of test compounds are evaluated in mice using conventional methods, using oral (25 mg/kg), intraperitoneal (25 mg/kg), and intravenous routes (5 mg/kg) of administration. The following approximate C$_{max}$ (ng/mL) values for test compounds are determined.

| Example | Oral C$_{max}$ | IP C$_{max}$ | IV C$_{max}$ |
|---|---|---|---|
| 5a | 200 | 2000 | 200 |
| 5e | 500 | 100 | 200 |

EXAMPLE. Pancreatic Cancer Cell Xenograft. PaCa-2 cells (2.5×10$^6$) in 0.2 mL of DMEM media were implanted s.c. into the right flanks of NOD/SCID mice. Test compounds are dissolved in 4% CremophorEL:EtOH (1:1)/saline solution or methylcellulose (0.5%, Sigma). When tumor volumes are greater than about 100 mm$^3$, test compounds are administered, such as orally, twice daily, 8 hours apart, at 25 mg/kg for 10 to 18 days (5 days on 2 days off schedule). Tumors are measured biweekly and followed for approximately 6 weeks. Tumor volumes are monitored by caliper measurement [tumor volume=length×(perpendicular width) 2×0.5] and the average tumor volume in mm$^3$ for each treatment group is plotted. Treatment corresponds to days 1 to 15. Average tumor volume±SE for the vehicle compared to test compounds (n=7) are analyzed by statistical analysis. Additional details are described in Fishel et al. Mol Cancer Ther. 2011 September;10(9):1698-708. When administered orally at 25 mg/kg twice daily, for 18 days, Compound 6a showed significant reduction in tumor volume compared to untreated control, as shown in FIG. 1.

What is claimed is:

1. A method for treating a disease responsive to Ape1 inhibition in a host animal, the method comprising administering to the host animal a composition comprising a therapeutically effective amount of a compound of the formula

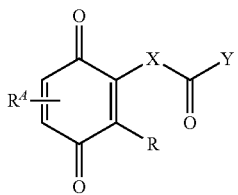

or a pharmaceutically acceptable salt thereof, wherein:
$R^4$ represents a fused aryl ring that is optionally substituted;
R is hydrogen or halo, or alkyl, heteroalkyl, cycloalkyl, cycloheteroalkyl, alkoxy, heteroalkoxy cycloalkoxy, cycloheteroalkoxy, alkylthio, heteroalkylthio cycloalkylthio, or cycloheteroalkylthio, each of which is optionally substituted;
X is alkylene, alkenylene, or alkynylene, each of which is optionally substituted; and
Y is $N(R^1)_2$, $NHOR^2$, or $NR^2 OR^2$, where each $R^1$ is independently selected from the group consisting of alkyl, heteroalkyl, cycloalkyl, and cycloheteroalkyl, each of which is optionally substituted, or both $R^1$ are taken together with the attached nitrogen to form an optionally substituted heterocycle; where each $R^2$ is independently selected from the group consisting of hydrogen, alkyl, heteroalkyl, cycloalkyl, and cycloheteroalkyl, each of which is optionally substituted, and a prodrug group, or both $R^2$ are taken together with the attached nitrogen and oxygen to form an optionally substituted heterocycle.

2. The method of claim 1, wherein $R^4$ represents optionally substituted benzo.
3. The method of claim 1, wherein R is alkyl or heteroalkyl, each of which is optionally substituted.
4. The method of claim 1, wherein R is optionally substituted alkyl.
5. The method of claim 1, wherein R is alkoxy.
6. The method of claim 1, wherein R is alkylthio.
7. The method of claim 1, wherein R is halo.
8. The method of claim 1, wherein each $R^1$ is optionally substituted alkyl.
9. The method of claim 1, wherein one $R^1$ is polyhydroxyalkyl.
10. The method of claim 1, wherein both $R^1$ are taken together with the attached nitrogen to form an optionally substituted heterocycle selected from the group consisting of pyrrolidine, piperidine, piperazine, morpholine, pyrrolidinone, piperidinone, piperazinone, and morpholinone.
11. The method of claim 1, wherein at least one $R^2$ is hydrogen.
12. The method of claim 1, wherein at least one $R^2$ is alkyl.
13. The method of claim 1, wherein both $R^2$ are alkyl.
14. The method of claim 1, wherein both $R^2$ are taken together with the attached nitrogen and oxygen to form an optionally substituted heterocycle selected from the group consisting of oxazolidine, oxazine, oxazapine, oxazolidinone, oxazinone, and oxazapinone.
15. The method of claim 1, wherein X is optionally substituted alkylene.
16. The method of claim 1, wherein X is optionally substituted alkenylene.
17. The method of claim 1, wherein X is optionally substituted alkynylene.
18. The method of claim 1, wherein the compound has the formula

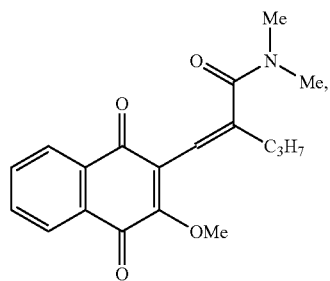

or a pharmaceutically acceptable salt thereof.

19. The method of claim 1, wherein the compound has the formula

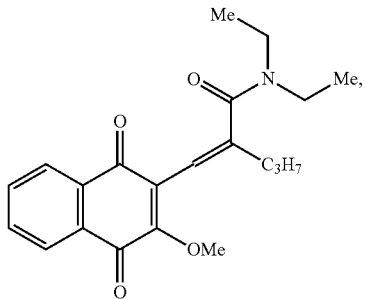

or a pharmaceutically acceptable salt thereof.

20. The method of claim 1, wherein the compound has the formula

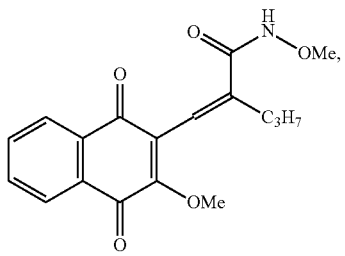

or a pharmaceutically acceptable salt thereof.

* * * * *